United States Patent [19]

Kaneko et al.

[11] Patent Number: 4,642,352

[45] Date of Patent: Feb. 10, 1987

[54] ACYLAMINO MITOSANES

[75] Inventors: Takushi Kaneko; Henry S. L. Wong; Terrence W. Doyle, all of Fayetteville, N.Y.

[73] Assignee: Bristol-Myers Company, New York, N.Y.

[21] Appl. No.: 564,806

[22] Filed: Dec. 23, 1983

[51] Int. Cl.$^4$ .................. C07D 487/14; A61K 31/40
[52] U.S. Cl. ................................... 548/422; 548/414
[58] Field of Search ............................. 548/414, 422

[56] References Cited

U.S. PATENT DOCUMENTS

| | | | |
|---|---|---|---|
| 3,332,944 | 7/1967 | Cosulich et al. | 548/422 X |
| 3,420,846 | 1/1969 | Matsui et al. | 548/422 |
| 3,450,705 | 6/1969 | Matsui et al. | 548/422 X |
| 3,514,452 | 5/1970 | Matsui et al. | 548/422 |
| 3,660,578 | 5/1972 | Hata et al. | 548/422 X |
| 4,231,936 | 11/1980 | Nakano et al. | 548/422 |
| 4,268,676 | 5/1981 | Remers | 548/422 |
| 4,444,768 | 4/1984 | Renner et al. | 424/251 |
| 4,487,769 | 12/1984 | Vyas et al. | 548/422 X |

FOREIGN PATENT DOCUMENTS 771155 11/1967 Canada ............................... 548/414

OTHER PUBLICATIONS

Burger, ed., *Medicinal Chemistry*, 2nd ed., Interscience Publishers, N.Y., (1960), p. 125.
Greene, *Protective Groups in Organic Synthesis*, John Wiley & Sons (1981), pp. 224, 232, 239, 250-254, 261, 281-282.
March, *Advanced Organic Chemistry*, 2d ed., McGraw Hill, N.Y. (1977), pp. 382-383.
McOmie, ed., *Protective Groups in Organic Chemistry*, Plenum Press, (1973), p. 73.
Slavik et al., Chemical Abstracts, vol. 91, 1979, entry 22426z.
Physicians' Desk Reference 35th Ed., 1981, pp. 717-718.
J. Amer. Chem. Soc. 84, 3185-3187 (1962).
Matsui et al., "The Journal of Antibiotics", XXI, 189-198 (1968).
Kinoshita et al., "J. Med. Chem." 14, 103-109 (1971).
Iyengar et al., "J. Med. Chem." 24, 975-981 (1981).
Iyengar, Sami, Remers, and Bradner, Abstracts of Papers, Abstract No. MEDI 72.
Sasaki et al., Internat. J. Pharm., 1983, 15, 49-59.
Claridge et al., Abst. of the Annual Meeting of Amer. Soc. for Microbiology 1982, Abs. 028.
A. F. Wagner et al., Antibiot Chemother, vol. 12, 464-468 (1962).
Cheng et al., J. Med. Chem. 20, 767-770 (1977).
H. Sasaki et al., International Journal of Pharmaceutics, 15 (1983) 61-71.
H. Sasaki et al., Chem. Pharm. Bull. 31 (11), 4083-4090 (1983).

*Primary Examiner*—Mark L. Berch
*Assistant Examiner*—William A. Teoli, Jr.
*Attorney, Agent, or Firm*—Robert E. Carnahan

[57] ABSTRACT

7-Acylamino-9a-methoxymitosanes having enhanced capacity to inhibit animal tumors in vivo relative to mitomycin C are produced by $N^7$-acylation of 7-amino-9a-methoxymitosane, or $N^{1a},N^7$-diacylation thereof. Carboxamide, thiocarboxamide, urea, thiourea, urethane, thiophosphoramide, phosphoramide, and sulfonamide derivatives are disclosed.

23 Claims, No Drawings

ACYLAMINO MITOSANES

FIELD OF THE INVENTION

The present invention refers to mitomycin analogs containing one or more acylamino groups (Class 260 Subclass 326.24). These compounds are mitomycin C derivatives in which either, or both, of the 7-amino group and the $N^{1a}$-nitrogen atom are incorporated within an acylamino substituent. These compounds are active antitumor substances having in vivo tumor inhibitor activity against experimental animal tumors.

Nomenclature—The systematic Chemical Abstracts name for mitomycin C is:

[1aR-(1aα,8β,8aα,8bα)]-6-amino-8-[((aminocarbonyl)oxy)methyl]-1,1a,2,8,8a,8b-hexahydro-8a-methoxy-5-methyl-azirino[2',3',3,4[pyrrolo]1,2-a]indole-4,7-dione according to which the azirinopyrroloindole ring system is numbered as follows:

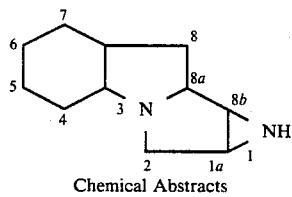

Chemical Abstracts

Formula I

A trivial system of nomenclature which has found wide use in the mitomycin literature identifies the foregoing ring system including several of the characteristic substituents of the mitomycins as mitosane.

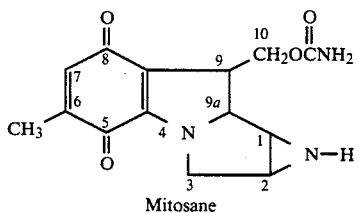

Mitosane

Formula II

While this system is convenient and appropriate for a number of simple derivatives such as those bearing substituents on the azirino ring nitrogen atom or in the 7- or 9a-positions, it suffers from certain ambiguities and shortcomings for general use. With regard to the compounds of the present invention which are mitomycin C derivatives having substituents on both the azirino ring nitrogen atom and on the aromatic ring amino nitrogen atom, we have chosen in the present specification to refer to the azirino nitrogen atom as $N^{1a}$ and the aromatic ring amino nitrogen atom as $N^7$ in using the mitosane nomenclature system. As to the stereochemical configuration of the products of this invention, it is intended when identifying them by the root name "mitosane" or by structural formula to identify the stereochemical configuration thereof as the same as that of mitomycin C.

DESCRIPTION OF THE PRIOR ART

Mitomycin C is an antibiotic which is produced by fermentation and is presently on sale under Food and Drug Administration approval in the therapy of disseminated adenocarcinoma of the stomach or pancreas in proven combinations with other approved chemotherapeutic agents and as palliative treatment when other modalities have failed (Mutamycin ® Bristol Laboratories, Syracuse, N.Y. 13201, Physicians' Desk Reference 35th Edition, 1981, pp. 717 and 718). Mitomycin C and its production by fermentation is the subject of U.S. Pat. No. 3,660,578 patented May 2, 1972 claiming priority from earlier applications including an application filed in Japan on Apr. 6, 1957.

The structures of mitomycins A, B, C, and of porfiromycin were first published by J. S. Webb et al. of Lederle Laboratories Division American Cyanamid Company, J. Amer. Chem. Soc. 84, 3185–3187 (1962). One of the chemical transformations used in this structure study to relate mitomycin A and mitomycin C was the conversion of the former, 7,9α-dimethoxymitosane, by reaction with ammonia to the latter, 7-amino-9α-methoxymitosane. Displacement of the 7-methoxy group of mitomycin A has proven to be a reaction of considerable interest in the preparation of antitumor active derivatives of mitomycin C. The following articles and patents each deals with the conversion of mitomycin A to a 7-substituted amino mitomycin C derivative having antitumor activity. The prior art, however, has not provided any example of a 7-acylamino mitomycin C analog of the sort provided by the present invention.

Matsui et al. "The Journal of Antibiotics", XXI, 189–198 (1968).

Kinoshita et al. "J. Med. Chem." 14, 103–109 (1971).

Iyengar et al. "J. Med. Chem." 24, 975–981 (1981).

Iyengar, Sami, Remers, and Bradner, Abstracts of Papers Annual Meeting of the American Chemical Society, Las Vegas, Nev., March 1982, Abstract No. MEDI 72.

Sasaki, et al. Internat. J. Pharm., 1983, 15, 49.

The following patents deal with the preparation of 7-substituted aminomitosane derivatives by the reaction of mitomycin A, mitomycin B, or an $N^{1a}$-substituted derivative thereof with a primary or secondary amine:

Cosulich et al. U.S. Pat. No. 3,332,944 patented July 25, 1967.

Matsui et al. U.S. Pat. No. 3,420,846 patented Jan. 7, 1969.

Matsui et al. U.S. Pat. No. 3,450,705 patented June 17, 1969.

Matsui et al. U.S. Pat. No. 3,514,452 patented May 26, 1970.

Nakano et al. U.S. Pat. No. 4,231,936 patented Nov. 4, 1980.

Remers U.S. Pat. No. 4,268,676 patented May 19, 1981.

Mitomycin C derivatives having a substituted amino substituent in the 7-position have also been prepared by directed biosynthesis, that is by supplementing fermentation broths with a series of primary amines, and carrying out the conventional mitomycin fermentation (C. A. Claridge et al. Abst. of the Annual Metting of Amer. Soc. for Microbiology 1982. Abs. 028).

SUMMARY OF THE INVENTION

This invention is concerned with a still further group of $N^7$-substituted mitomycin C derivatives in which the amino group in the 7-position is substituted by an organic acyl group. Carboxamides, thiocarboxamides, ureas, thioureas, urethanes, thiophosphoramides, phosphoramides, and sulfonamides are illustrated. These compounds conform to the following formula:

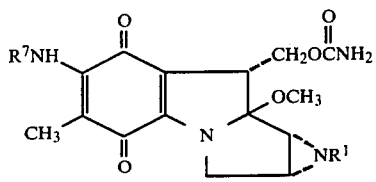

Formula III wherein
R$^1$ is selected from H, C$_{1-6}$ alkyl, and R$^7$,
R$^7$ is selected from

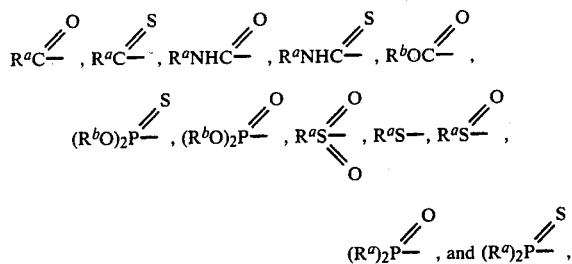

wherein
R$^a$ is selected from H, C$_{1-6}$ alkyl, A-substituted C$_{1-6}$ alkyl, C$_{6-10}$ aryl, A-substituted C$_{6-10}$ aryl, C$_{7-17}$ aralkyl, A-substituted C$_{7-17}$ aralkyl, C$_{2-6}$ alkenyl, A-substituted C$_{2-6}$ alkenyl, C$_{2-6}$ alkynyl, A-substituted C$_{2-6}$ alkynyl, C$_{3-8}$ cycloalkyl, C$_{4-10}$ cycloalkylalkyl,
R$^b$ is selected from the group consisting of C$_{1-6}$ alkyl, A-substituted C$_{1-6}$ alkyl, C$_{6-10}$ aryl, A-substituted C$_{6-10}$ aryl, C$_{7-17}$ aralkyl and A-substituted C$_{7-17}$ aralkyl,
wherein said A substituent is selected from the group consisting of chlorine, bromine, fluorine, iodine, amino, protected amino, C$_{1-6}$ alkoxy, C$_{1-6}$ alkylamino, di(C$_{1-6}$)alkylamino, C$_{3-8}$ cycloalkylamino, C$_{4-14}$ cycloalkylamino, thiol, C$_{1-6}$ alkylthio, C$_{1-6}$ alkyldithio, C$_{6-10}$ arylthio, and C$_{7-17}$ aralkylthio.

These compounds are inhibitors of experimental tumors in animals. They are comparable to mitomycin C with respect to the types of tumors which they inhibit, but in many instances possess higher activity in the sense that they exert a greater degree of inhibition than can be achieved with mitomycin C. Their toxicity is generally less than that of mitomycin C reflected particularly in their lower myelosuppressive action. For antitumor purposes, they are administered to a mammal bearing a tumor in substantially non-toxic antitumor effective dose.

They are administered primarily by injection in much the same way as mitomycin C. Generally they may be employed in higher doses than mitomycin C in view of their reduced toxicity and increased antitumor inhibitory effect at the higher doses. They are readily distributed as dry pharmaceutical compositions containing diluents, buffers, stabilizers, solubilizers, and ingredients contributing to pharmaceutical elegance. These compositions may be constituted with an injectable liquid extemporaneously just prior to use. Suitable injection liquids include water, isotonic saline, etc.

DETAILED DESCRIPTION OF THE INVENTION

The compounds of Formula III are prepared from mitomycin C by first deprotonation to provide the anionic form of mitomycin C followed by reaction of the anion with an organic isocyanate or isothiocyanate to provide a mitosane having a substituted ureido or thioureido group in the 7-position or by reaction of the anionic form of mitomycin C with an acylating form of an organic acid such as an acyl halide, a reactive ester of a carboxylic or thiocarboxylic acid such as a phenyl, p-nitrophenyl, p-nitrobenzyl, etc. ester or with an ester of a carboxylic acid with a N-hydroxyamine such as N-hydroxysuccinimide, N-hydroxybenzotriazole, N-hydroxyphthaimide, N-hydroxypiperidine, etc., an organic carbonate, or an organic haloformate to provide a mitosane having an amido group, or carbamoyl group in the 7-position. The acyl anhydrides may be also be employed as acylating agents.

The acylating agents for reaction with anionic mitomycin C are characterized by the following formulas:

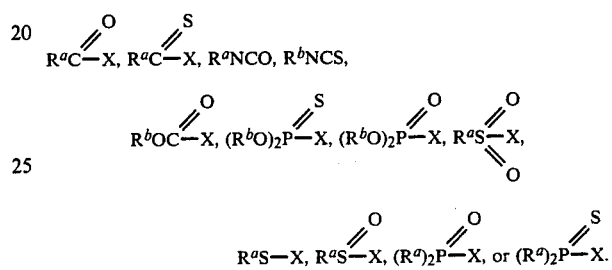

In these formulas X is a group which has come to be known in the art as a leaving group. A great variety of such groups have been established in the field of organic synthesis and they include the halides and various other reactive esters such as those listed above as well as other acyl group in which event the resulting acylating agent is an anhydride. Mixed anhydrides may be used in which one portion of the anhydride becomes the acylating function and the other the leaving group.

The deprotonation of mitomycin C to provide the anionic form thereof having nucleophilic properties was first disclosed in co-pending application Ser. No. 492,903 filed May 9, 1983, and U.S. Pat. No. 4,487,769. In this form, mitomycin C readily reacts with electrophilic reagents, in this instance acylating agents.

Conditions for the deprotonation of mitomycin C involve treatment thereof in dimethylformamide solution with about 1.5 molar proportions of sodium hydride at room temperature, or lower. The reaction of the anion with an acylating agent, at least one chemical equivalent thereof and preferably from 1.5 to 2 chemical equivalents thereof relative to the anionic form of mitomycin C, is carried out under anhydrous conditions at a temperature of from about room temperature to about $-60°$ C. Temperatures of $-20°$ to $-30°$ C. are readily achieved under both laboratory and manufacturing conditions and are quite satisfactory for conduct of the present process.

Aprotic polar organic solvents such as pyridine, dimethylformamide, hexamethylphosphoramide, or dimethylsulfoxide are employed. The method is not, however, limited to formation of anionic mitomycin in the fashion described above since modifications will occur to those skilled in the art.

Preferred compounds of the present invention, because of their high antitumor activity and relatively low toxicity compared to mitomycin C, are 7-(formyl)amino-9a-methoxymitosane (Example 1), 7-(acetyl- )amino-9-methoxymitosane (Example 3), and 7-(cyclopropanecarbonyl)amino-9a-methoxymitosane (Example 13). These compounds are representative of the subclass having Formula III in which $R^7$ is alkanoyl having 1 to 7 carbon atoms or cycloalkylcarbonyl having 4 to 9 carbon atoms which include the preferred substances of the present invention.

Activity Against P-388 Murine Leukemia

Table I contains the results of laboratory tests with $CDF_1$ female mice implanted intraperitoneally with a tumor inoculum of $10^6$ ascites cells of P-388 murine leukemia and treated with various doses of either a test compound of this invention, or with mitomycin C. The compounds were administered by intraperitoneal injection. Groups of six mice were used for each dosage amount and they were treated with a single dose of the compound on the day of inoculation. A group of ten saline treated control mice was included in each series of experiments. The mitomycin C treated groups were included as a positive control. A 30 day protocol was employed with the mean survival time in days being determined for each group of mice and the number of survivors at the end of the 30 day period being noted. The mice were weighed before treatment and again on day six. The change in weight was taken as a measure of drug toxicity. Mice weighing 20 grams each were employed and a loss in weight of up to approximately 2 grams was not considered excessive. The results were determined in terms of % T/C which is the ratio of the mean survival time of the treated group to the mean survival time of the saline treated control group times 100. The saline treated control animals usually died within nine days. The "maximum effect" in the following Table is expressed as % T/C and the dose giving that effect is given. The values in parenthesis are the values obtained with mitomycin C as the positive control in the same experiment. Thus a measure of the relative activity of the present substances to mitomycin C can be estimated. A minimum effect in terms of % T/C was considered to be 125. The minimum effective dose reported in the following Table is that dose giving a % T/C of approximately 125. The two values given in each instance in the "average weight change" column are respectively the average weight change per mouse at the maximum effective dose and at the minimum effective dose.

TABLE I

| | Inhibition of P-388 Murine Leukemia | | | |
|---|---|---|---|---|
| Compound of Example No. | Maximum Effect % T/C | dose[1] | Minimum effective dose[1] | Average weight change[2] |
| 1 | 183(144)[3] | 3.2(3.2)[3] | 1.6 | −2.1,−1.3 |
|   | 244(228) | 6.4(4.8) | <0.4 | −2.2,+0.3 |
| 2 | 183(228) | 6.4(4.8) | 0.8 | −1.0,+0.5 |
| 6 | 183(228) | 12.8(4.8) | 0.8 | −0.8,+0.4 |
| 5 | 219(263) | 25.6(4.8) | 0.8 | −2.8,−1.3 |
| 3 | 233(228) | 6.4(3.2) | 0.2 | −1.4,+0.3 |
| 13 | 250(228) | 12.8(3.2) | 0.2 | −1.8,+0.4 |
| 14 (BL-6938) | 163(363) | 3.2(4.8) | <0.2 | −0.6,+0.6 |
| 11 | 200(244) | 6.4(4.8) | <0.2 | −2.2,−1.4 |
| 10 | 189(356) | 6.4(4.8) | <0.2 | −1.2,−0.3 |
| 7 | 213(313) | 3.2(3.2) | <0.1 | −0.3,+0.6 |
| 9 | 206(313) | 3.2(3.2) | <0.025 | −1.8,+2.3 |
| 15 | inactive | | | |

TABLE I-continued

| | Inhibition of P-388 Murine Leukemia | | | |
|---|---|---|---|---|
| Compound of Example No. | Maximum Effect % T/C | dose[1] | Minimum effective dose[1] | Average weight change[2] |
| 8 | 229(241) | 3.2(4.8) | <0.2 | −1.6,−0.9 |

[1]mg. per kg. of body weight.
[2]grams per mouse, at maximum and minimum effective doses.
[3]values given in parentheses are for mitomycin C.

Table II contains results of antitumor tests using the B16 melanoma grown in mice. $BDF_1$ mice were employed and inoculated subcutaneously with the tumor implant. A 60 day protocol was used. Groups of ten mice were used for each dosage amount tested and the mean survival time for each group was determined. Control animals inoculated in the same way as the test animals and treated with the injection vehicle and no drug exhibited a mean survival time of 24.5 days. The survival time relative to that of the controls (% T/C) was used as a measure of effectiveness, and the maximal effective dose and minimal effective dose for each test compound was determined. The minimal effective dose was defined as that dose exhibiting a % T/C value of 125. For each dosage level, the test animals were treated with the test compound on days 1, 5, and 9 by the intravenous route.

TABLE II

| | B16 Melanoma | | | |
|---|---|---|---|---|
| Compound of Example No. | Maximum Effect % T/C | Dose[1] | Minimum Effective Dose[1] | Average Wt. Change[2] |
| 1 | 228(195)[3] | 2(4)[3] | <1 | −0.6,+0.2 |
|   | 220(220) | 2(4) | <0.5 | −2.8,−1.1 |
| 3 | 186(195) | 1(4) | <1 | +0.6,+0.6 |

[1]mg. per kg. of body weight.
[2]grams per day per mouse.
[3]values in parentheses are for mitomycin C tested in the same run.

Table III contains further results of antitumor tests using the B16 melanoma grown in $BDF_1$ mice, this time inoculated intraperitoneally with the tumor (0.5 ml., 10% brei). A 60 day protocol was used. Groups of ten mice were used for each dosage amount tested and the mean survival time for each group was determined. Control animals inoculated in the same way as the test animals and treated with the injection vehicle and no drug exhibited a mean survival time of 20.5 days. The survival time relative to that of the controls (% T/C) was used as a measure of effectiveness, and the maximal effective dose and minimal effective dose for each test compound was determined. The minimal effective dose was defined as that dose exhibiting a % T/C value of 125. For each dosage level, the test animals were treated with the test compound on days 1, 5, and 9 by the intraperitoneal route.

TABLE III

| | B16 Melanoma | | | |
|---|---|---|---|---|
| Compound of Example No. | Maximum Effect % T/C | Dose[1] | Minimum Effective Dose[1] | Average Wt. Change[2] |
| 3 | >249(173)[3] | 4(2) | <0.5 | −0.4, none |
| 13 | 173(173) | 1.5(2) | <1.5 | none, none |
| 16 | >270(202) | 7.0(3) | <7.0 | +1.2, 1.2 |

[1]mg. per kg. of body weight.
[2]grams per day per mouse.
[3]values in parentheses are for mitomycin C tested in the same run.

Table IV refers to the measurement of myelosuppressive effect of the compounds of Examples 1, 3, and 13 when administered intravenously to mice in comparison to mitomycin C. The mice were given a single dose of test compound on Day 0 and total white blood cell counts (WBC) were taken on Days 0, 4, and 7. The values for Days 4 and 7 are reported in Table IV as percent change (Δ%). Differential counts were made on Days 0 and 4 and reported as percent change (Δ%) on Day 4. Various doses of test compounds, as shown in the table, were given to different groups of 10 animals. The values for Δ% given in parentheses are comparison values for mitomycin C measured in the same way. The compounds of Examples 1, 3, and 13 were concluded to be less myelosuppressive than mitomycin C. At doses having equivalent lethality, the present compounds have substantially less effect on neutrophil counts than mitomycin C.

EXAMPLE 1

7-(Formyl)amino-9a-methoxymitosane (BL-6859)

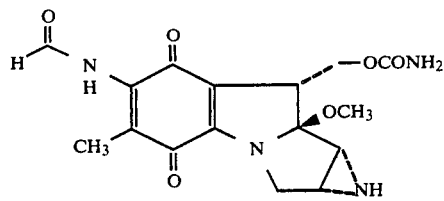

Dimethylformamide (6 mL) was added to a mixture of mitomycin C (549 mg, 1.78 mmol) and 214 mg of 50% oil dispersion of NaH (4.45 mmol) maintained in an atmosphere of argon. After stirring at room temperature for 10 minutes, the mixture was cooled to −20° C.

TABLE IV

| | | Myelosuppressive and Lethal Toxicity | | | | |
|---|---|---|---|---|---|---|
| Compound of Example No. | Dose mg/kg. i.v. | Day 4 WBC Δ % | Day 4 Neutrophils Δ % | Day 4 Lymphocytes Δ % | Day 7 WBC Δ % | Deaths By Day 14 |
| 3 | 12.8 | −69 | — | — | 5/5 dead | 5/5 |
|   | 6.4  | −57(−82)[1] | −5(−96)[1] | −65(−80)[1] | −15(−58)[1] | 1/10 |
|   | 3.2  | −26(−54) | +11(−62) | −30(−53) | −18(−16) | 0/10 |
| 1 | 12.8 | −83 | | | 5/5 dead | 5/5 |
|   | 6.4  | −77(−71) | | | 10/10 dead | 10/10 |
|   | 3.2  | −62(−43) | −25(−77) | −69(−35) | −22(−8) | 6/10 |
| 13 | 12.8 | −64 | +6 | −78 | −14 | 10/10 |
|    | 6.4  | −26(−78) | −2(−96) | −31(−75) | +18(−57) | 0/10 |

[1]values shown in parentheses are for mitomycin C measured under comparable conditions.

DESCRIPTION OF SPECIFIC EMBODIMENTS

The following examples constitute detailed procedures for the preparation of various specific embodiments of the present invention. The compounds were generally characterized by their nuclear magnetic resonance, infra red absorption, and ultra violet absorption spectra. The spectra are described in the following examples in conventional terms which are accepted in the art for this type of data. In most instances, elemental analyses are given which conform to the structural formulas shown lending further confirmation to the identity of these substances. The following is a glossary of the abbreviations employed.

Abbreviations and Glossary

BOC—tert.-butoxycarbonyl
DMF—dimethylformamide
dry ice—solid carbon dioxide
EtOAc—ethyl acetate
IR—infra red absorption spectrum
MeOH—methanol
NMR—H nuclear magnetic resonance spectrum
RT—room temperature, 20°–25° C.
UV—ultra violet absorption spectrum and phenyl formate (0.60 mL of 65% pure material, 3.50 mmol, H. L. Yale, J. Org. Chem. 36, 3234 (1971)) was added. The reaction mixture was stirred at −20° C. for 30 minutes and then warmed up to room temperature over a period of 1 hour. After quenching the reaction by the addition of solid $CO_2$, the reaction mixture was diluted with EtOAc. The resulting precipitate was filtered off and the solvent was removed under reduced pressure. The residue was chromatographed on silica gel (5% MeOH—$CH_2Cl_2$) to give the title compound (306 mg, 47%). A portion of this material was crystallized from acetone and ether: mp>280° C.; NMR (pyridine-$d_5$,δ) 2.02(s, 3H), 2.72(m, 1H), 3.06(m, 1H), 3.24(s, 3H), 3.50(dd, 1H, J=12, 1 Hz), 3.93(dd, 1H, J=10, 4 Hz), 4.16(d, 1H, J=12 Hz), 4.92(t, 1H, J=10 Hz), 5.24(dd, 1H, J=10, 4 Hz), 8.76(s, 1H); IR(KBr) 3450, 3300, 1705, 1660, 1580, 1336, 1220, 1063 cm$^{-1}$; UV (MeOH, $\lambda_{max}$) 223, 330, 520 nm.

Anal. Calc'd. for $C_{16}H_{18}N_4O_6$: C, 53.04; H, 5.01; N, 15.46. Found: C, 52.75; H, 5.09; N, 15.96.

By substitution of phenyl thioacetate, or ethyl thioformate for phenyl formate in this example, 7-(thioacetyl or thioformyl)amino-9a-methoxymitosane may be produced.

EXAMPLE 2

7-(Trifluoroacetyl)amino-9a-methoxymitosane (BL-6878)

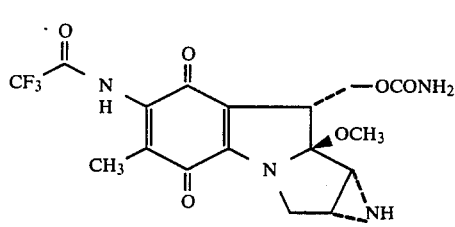

Starting with 300 mg (0.899 mmol) of mitomycin C and 2.25 mmol of NaH, the reaction was carried out as described in Example 1. p-Nitrophenyl trifluoroacetate (432 mg, 1.80 mmol) was used as the acylating agent. A silica gel TLC (10% MeOH—$CH_2Cl_2$) gave the title compound as a reddish purple amorphous solid (91 mg, 24%): mp 93°–95° C.; NMR (pyridine-$d_5$,δ) 2.02(s, 3H), 2.74(m, 1H), 3.11(d, 1H, J=4 Hz), 3.20(s, 3H), 3.52(dd, 1H, J=12, Hz), 4.00(dd, 1H, J=11, 5 Hz), 5.00(t, 1H, J=10 Hz), 5.35(dd, 1H, J=10, 5 Hz); IR(KBr) 3460, 3300, 1720, 1665, 1580, 1335, 1220, 1150, 1065 cm$^{-1}$; UV (MeOH,$\lambda_{max}$) 216, 355, 510 nm. A substantial amount (120 mg) of the starting material was also recovered.

Anal. Calc'd. for $C_{17}H_{17}F_3N_4O_6$: C, 47.45; H, 3.98; N, 13.01. Found: C, 48.10; H, 4.43; N, 12.91.

EXAMPLE 3

7-(Acetyl)amino-9a-methoxymitosane (BL-6905)

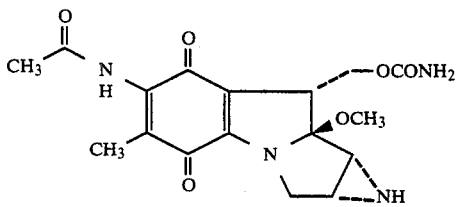

Starting with 668 mg (2 mmol) of mitomycin C and 4 mmol of NaH, the reaction was carried out similarly to Example 1. The N-hydroxysuccinimide ester of acetic acid (314 mg, 2 mmol) was employed as the acylating agent. A flash chromatography on silica gel (3% MeOH—$CH_2Cl_2$) gave 200 mg (27%) of the title compound: mp 110°–112° C., NMR (pyridine-$d_5$,δ) 2.06(s, 3H), 2.39(s, 3H), 2.75(m, 1H), 3.12(d, 1H, J=4 Hz), 3.24(s, 3H), 3.52(dd, 1H, J=13, 1 Hz), 3.95(dd, 1H, J=10, 4 Hz), 4.19 (d, 1H, J=13 Hz), 5.03(t, 1H, J=10 Hz), 5.34(dd, 1H, J=10, 4 Hz), 10.16(bs, 1H); IR(KBr) 3420, 3320, 1700, 1650, 1610, 1575, 1330, 1245, 1055 cm$^{-1}$; UV ($CH_2OH$, $\lambda_{max}$) 220, 330, 510 nm.

Anal. Calc'd. for $C_{17}H_{20}N_4O_6.H_2O$: C, 51.77; H, 5.62; N, 14.21. Found: C, 51.58; H, 5.25; N, 14.10.

EXAMPLE 4

7-(2-Chloroacetyl)amino-9a-methoxymitosane (BL-6904)

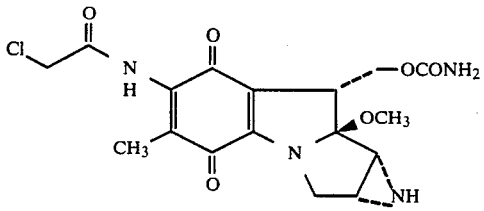

Starting with 668 mg (2 mmol) of mitomycin C and 4 mmol of NaH, the reaction was carried out similarly to Example 1. Phenyl chloroacetate (520 mg, 3 mmol) was employed as the acylating agent. A silica gel chromatography (5% MeOH—$CH_2Cl_2$) gave 60 mg (7.3%) of the title compound: mp 118°–120° C.; NMR (pyridine-$d_5$,δ) 2.04(s, 3H), 2.77(m, 1H), 3.15(d, 1H, J=4 Hz), 3.53(dd, 1H, J=12, 1 Hz), 4.04(dd, 1H, J=11, 4 Hz), 4.64(s, 2H), 5.01(t, 1H, J=10 Hz), 5.31(dd, 1H, J=10, 4 Hz); IR(KBr) 3420, 3330, 1760, 1647, 1588, 1480, 1330, 1060 cm$^{-1}$; UV (MeOH, $\lambda_{max}$) 218, 235 (sh), 298 (sh), 342 480 nm. Approximately 100 mg of the starting material was also recovered.

Anal. Calc'd. for $C_{17}H_{19}ClN_4O_6$: C, 49.70; H, 4.66; N, 13.64. Found: C, 51.31; H, 5.05; N, 11.75.

EXAMPLEP 5

7-(Methanesulfonyl)amino-9a-methoxymitosane (BL-6885)

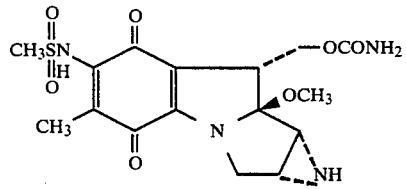

Dimethylformamide (6 mL) was added to a mixture of mitomycin C (668 mg, 2 mmol) and 4 mmol of NaH under an atmosphere of argon. After stirring at room temperature for 20 minutes, the reaction mixture was cooled to −25° C. and p-nitrophenyl methanesulfonate (454 mg, 2 mmol, Kametani et al. Yakugaku Zasshi, 84, 237 (1963)) was added. The reaction mixture was kept at −25° C. for 4 hours. After quenching the reaction with solid $CO_2$, the reaction mixture was diluted with EtOAc and washed with brine. Drying over $Na_2SO_4$ and removal of the solvent gave a reddish purple residue. It was chromatographed on neutral alumina (3% MeOH-$CH_2Cl_2$) to give 100 mg (12%) of the title compound: mp 126°–128° C.; NMR (pyridine-$d_5$, δ) 2.28 (s, 3H), 2.74(m, 1H), 3.15(d, 1H, J=4 Hz), 3.24(s, 3H), 3.31(s, 3H), 3.55(dd, 1H, J=13, 1 Hz), 4.04(dd, 1H, J=11, 4 Hz), 4.19 (d, 1H, J=13 Hz), 5.06(t, 1H, J=11 Hz), 5.48(dd, 1H, J=11, 4 Hz); IR(KBr) 3450, 1710, 1650, 1600, 1445, 1335, 1155, 1060 cm$^{-1}$; UV (MeOH, $\lambda_{max}$) 218, 340, 360, 490, nm.

Anal. Calc'd for $C_{16}H_{19}N_4O_8S.H_2O$: C, 43.14; H, 4.75; N, 12.58. Found: C, 42.99; H, 4.67; N, 12.60.

EXAMPLE 6.

7-[3-(tert.-Butoxycarbonylamino)propionyl]amino-9a-methoxymitosane (BL-6879)

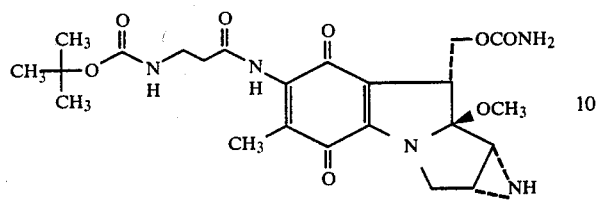

Starting with 350 mg (1.05 mmol) of mitomycin C and 2.62 mmol of NaH, the reaction was carried out similarly to Example 1. The N-hydroxysuccinimide ester of N-BOC-$\beta$-alanine was used as the acylating agent. A silica gel TLC (10% $CH_3OH$—$CH_2Cl_2$) provided 181 mg (34%) of the title compound: mp 121°–125° C.; NMR (pyridine-$d_5$,$\delta$) 1.53(s, 9H), 2.03(s, 3H), 2.75(m, 1H), 3.06(t, 2H, J=6 Hz), 3.11(m, 1H), 3.52(d, 1H, J=12 Hz), 3.81(q, 1H, J=6 Hz), 3.97(dd, 1H, J=10, 4 Hz), 4.16(d, 1H, J=12 Hz), 5.00(t, 1H, J=10 Hz), 5.30(dd, 1H, J=10, 4 Hz), 10.32(bs, 1H); IR(KBr) 3360, 3310, 1705, 1660, 1625, 1585, 1500, 1168, 1068 cm$^{-1}$; UV (MeOH, $\lambda_{max}$) 221, 237, 327, 515 nm.

Anal. Calc'd for $C_{23}H_{31}N_5O_8 \cdot H_2O$: C, 52.76; H, 6.35; N, 13.38. Found: C, 52.85; H, 6.22; N, 12.83.

EXAMPLE 7

7-(Methoxycarbonyl)amino-9a-methoxymitosane (BMY-25069)

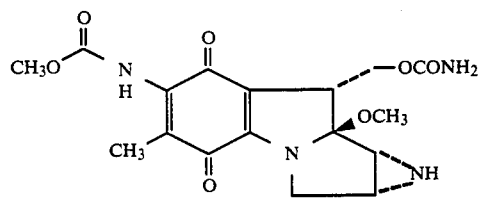

To a mixture of mitomycin C (334 mg, 1 mmol) and NaH 50% oil dispersion (96 mg, 2 mmol) was added under $N_2$ atmosphere 5 mL of dry DMF. The mixture was stirred at RT for 10 min and then cooled to $-30°$. Methyl p-nitrobenzyl carbonate (482 mg, 2.3 mmol) was added as a solid and stirring was continued for 1 h at $-30°$. The reaction was quenched by addition of a small amount of dry ice, and the reaction mixture was partitioned between EtOAc and water. The organic layer was washed with brine and dried over $Na_2SO_4$. The residue obtained after evaporation of the solvent was chromatographed on $SiO_2$ (2% $CH_3OH$—$CH_2Cl_2$) to give 150 mg (38%) of the title compound: mp 106°–107°; NMR (pyridine-$d_5$, $\delta$) 2.05(s, 3H), 2.76(m, 1H), 3.15(m, 1H), 3.54(d, 1H, J=12 Hz), 3.74(s, 3H), 4.04(dd, 1H, J=12, 5 Hz), 4.19(d, 1H, J=12 Hz), 5.12(t, 1H, J=12 Hz), 5.36(dd, 1H, J=10, 5 Hz), 10.20(bs, 1H); IR (KBr) 3450, 3300, 1725, 1652, 1615, 1580, 1495, 1445, 1335, 1220, 1010 cm$^{-1}$; UV ($CH_3OH$, $\lambda$max) 218, 329, 514 nm.

Anal. Calc'd for $C_{17}H_{20}N_4O_7$: C, 52.04; H, 5.14; N, 14.28. Found: C, 52.03; H, 5.15; N, 14.20.

EXAMPLE 8

7-(Ethoxycarbonyl)amino-9a-methoxymitosane (BMY-25082)

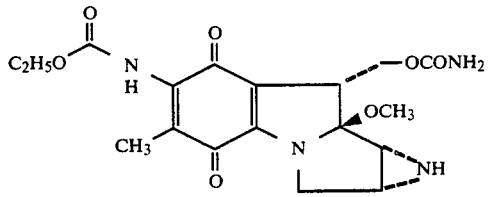

Starting with 334 mg (1 mmol) of mitomycin C, 96 mg of NaH 50% oil dispersion (2 mmol), and 450 mg ethyl p-nitrobenzyl carbonate, the title compound was prepared in a similar fashion as Example 7: 150 mg (37%); mp 100°–102°; NMR (pyridine-$d_5$, $\delta$) 1.16(t, 3H, J=7 Hz), 2.09(s, 3H), 2.77(m, 1H), 3.14(d, 1H, J=4 Hz), 3.26(s, 3H), 3.54(dd, 1H, J=13, 2 Hz), 4.02(dd, 1H, J=12, 5 Hz), 4.10(d, 1H, J=13 Hz), 4.12 (q, 2H, J=7 Hz), 5.10(t, 1H, J=12 Hz), 5.40(dd, 1H, J=10, 5 Hz): IR (KBr) 3460, 3300, 1740, 1655, 1620, 1580, 1495, 1335, 1220, 1060 cm$^{-1}$: UV ($CH_3OH$, $\lambda$max) 218, 330, 515 nm.

Anal. Calc'd for $C_{18}H_{22}N_4O_7 \cdot 0.75 H_2O$: C, 51.55; H, 5.64; N, 13.34. Found: C, 51.52; H, 5.64; N. 13.47.

EXAMPLE 9

7-[(2-Methoxyethoxy)carbonyl]amino-9a-methoxymitosane (BMY-25071)

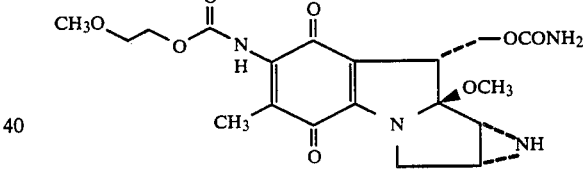

Starting with 668 mg (2 mmol) of mitomycin C, 192 mg of NaH 50% oil dispersion (4 mmol), and 960 mg (4 mmol) of 2-methoxyethyl p-nitrobenzyl carbonate, the title compound was prepared in a similar manner as Example 7: 300 mg (35%), mp 82°–84°; NMR (CDCl$_3$, $\delta$) 1.92(s, 3H), 2.90(m, 2H), 3.24(s, 3H), 3.45(s, 3H), 3.52–3.80(m, 4H), 4.11(d, 1H, J=12 Hz), 4.24–4.38(m, 2H), 4.44–4.84(m, 4H), 7.47(s, 1H): IR (KBr) 3450, 1715, 1655, 1585, 1505, 1450, 1340, 1225, 1065, cm$^{-1}$.

Anal. Calc'd for $C_{19}H_{24}N_4O_8 \cdot 0.25 H_2O$: C, 51.76; H, 5.60; N, 12.71. Found: C, 52.09; H, 5.50; N, 12.72.

EXAMPLE 10

7-(Isopropylaminocarbonyl)amino-9a-methoxymitosane (BMY-25003)

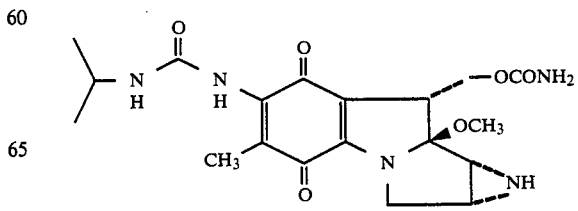

To a mixture of mitomycin C (668 mg, 2 mmol) and NaH 50% oil dispersion (192 mg, 4 mmol) was added under $N_2$ 8 mL of dry DMF. The resulting solution was stirred at room temperature for 20 min and then cooled to $-25°$. Isopropyl isocyanate (340 mg, 4 mmol) was added and stirring was continued at $-25°$ for 1 h. The reaction was quenched by addition of a small amount of dry ice, and the reaction mixture was partitioned between EtOAc and water. The organic layer was washed with brine and dried obher $Na_2SO_4$. The residue obtained after evaporation of the solvent was chromatographed on $SiO_2$ (3% $CH_3OH$—$CH_2Cl_2$) to give 140 mg (17%) of the title compound: mp 163°-165°; NMR (pyridine-d$_5$, δ) 1.19(d, 6H, J=6 Hz), 2.22(s, 3H), 2.75(m, 1H), 3.12(d, 1H, J=4 Hz), 3.22(s, 3H), 3.53(dd, 1H, J=12, 2 Hz), 3.94(dd, 1H, J=10, 5 Hz), 4.12(septet, 1H, J=6 Hz), 4.24(d, 1H, J=12 Hz), 4.75(t, 1H, J=10 Hz), 5.26(dd, 1H, J=10, 5 Hz), 7.80(d, 1H, J=7 Hz), 8.46(s, 1H): IR (KBr) 3340, 3300, 1700, 1630, 1455, 1320, 1215, 1050 cm$^{-1}$: UV ($CH_3OH$, λmax) 219, 238 (sh), 348, 520 nm.

Anal. Calc'd for $C_{19}H_{25}N_5O_6$ 0.75 $H_2O$: C, 52.71; H, 5.99; N, 16.17. Found: C, 53.01; H, 6.03; N, 15.86.

An earlier fraction gave 1a-(isopropylamiocarbonyl)-7-(isopropylaminocarbonyl)amino-9a-methoxymitosane: 120 mg (24%); NMR (pyridine-d$_5$, δ) 1.20(m, 12H), 2.22(s, 3H), 3.17(s, 3H), 3.40(m, 1H), 3.53(dd, 1H, J=12, 2 Hz), 3.78-4.30(m, 3H), 3.87(d, 1H, J=4 Hz), 4.16(d, 1H, J=12 Hz), 4.78(t, 1H, J=10 Hz), 5.30(dd, 1H, J=10, 4 Hz), 7.86(d, 1H, J=7 Hz), 8.40(s, 1H), 8.53(d, 1H, J=7 Hz).

EXAMPLE 11

7-(Cyclohexylaminocarbonyl)amino-9a-methoxymitosane (BMY-6936)

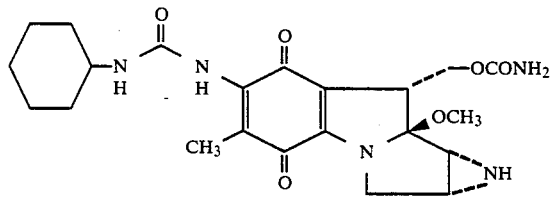

Starting with 334 mg (1 mmol) of mitomycin C, 96 mg of NaH 50% oil dispersion (2 mmol), and 250 mg (2 mmol) of cyclohexyl isocyanate, the title compound was prepared in a similar fashion as Example 10: 100 mg (22%); mp 138°-140°, NMR (pyridine-d$_5$, δ) 1.06-1.72(m, 10H), 1.96-2.15(m, 1H), 2.26(s, 3H), 2.75(bd, 1H, J=4 Hz), 3.12(d, 1H, J=4 Hz), 3.22(s, 3H), 3.56(d, 1H, J=13 Hz), 3.95(dd, 1H, J=12, 5 Hz), 4.27(d, 1H, J=13 Hz), 5.00(t, 1H, J=13 Hz), 5.28(dd, 1H, J=12, 5 Hz), 7.88(d, 1H, J=8 Hz), 8.52(s, 1H): IR (KBr) 3380, 1710, 1695, 1675, 1585, 1535, 1340, 1220, 1070 cm$^{-1}$: UV ($CH_3OH$, λmax) 218, 236 (sh), 348, 520 nm.

Anal. Calc'd for $C_{22}H_{29}N_5O_6$ 0.75 $H_2O$: C, 55.86; H, 6.50; N, 14.81. Found: C, 55.83; H. 6.22; N, 14.44.

An earlier fraction gave 70 mg (14%) of 1a-(cyclohexylaminocarbonyl)-7-(cylohexylaminocarbonyl)amino-9a-methoxymitosane: NMR (pyridine-d$_5$, δ) 1.1-1.7(m, 20 H), 1.9-2.2(m, 2H), 2.28(s, 3H), 3.19(s, 3H), 3.42(m, 1H), 3.54(dd, 1H, J=13, 2 Hz), 3.86(d, 1H, J=5 Hz), 3.94(dd, 1H, J=11, 5 Hz), 4.14(d, 1H, J-13 Hz), 4.78(t, 1H, J=11 Hz), 5.33(dd, 1H, J=11, 5 Hz), 7.94(d, 1H, J=7 Hz), 8.50(s, 1H), 8.64(d, 1H, J=7 Hz).

EXAMPLE 12

7-(Benzylaminocarbonyl)amino-9a-methoxymitosane (BL-6955)

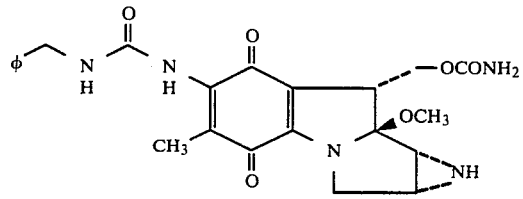

Starting with 668 mg (2 mmol) of mitomycin C 192 mg of NaH 50% oil dispersion (4 mmol), and 536 mg (4 mmol) of benzyl isocyanate, the title compound was prepared in a similar fashion as Example 10: 110 mg (12%); mp 145°-147°; NMR (pyridine-d$_5$, δ) 2.24(s, 3H), 2.74(m, 1H), 3.12(d, 1H, J=5 Hz), 3.23(s, 3H), 3.55(dd, 1H, J=13, 2 Hz), 3.96(dd, 1H, J=10, 5 Hz), 4.24(d, 1H, J=13 Hz), 4.68(d, 2H, J=6 Hz), 5.05(t, 1H, J=10 Hz), 5.27(dd, 1H, J=10, 5 Hz), 7.2-7.7(m, 5H), 8.5-8.7(m, 2H): IR (KBr) 3310, 1700, 1650, 1620, 1565, 1475, 1340, 1212, 1067 cm$^{-1}$: UV ($CH_3OH$, λmax) 217, 240 (sh), 346, 515 nm.

Anal. Calc'd for $C_{23}H_{25}N_5O_6$: C, 58.53; H, 5.45; N, 14.84. Found: C, 58.93; H, 5.45; N, 14.12.

EXAMPLE 13

7-(Cyclopropanecarbonyl)amino-9a-methoxymitosane (BL-6906)

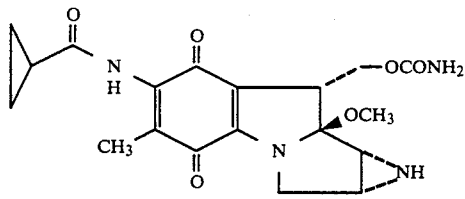

Starting with 668 mg (2 mmol) of mitomycin C, 4 mmol of NaH, and 370 mg (2 mmol) of N-hydroxysuccinimide ester of cyclopropane carboxylic acid, the reaction was carried out in a similar fashion to Example 1. A silica gel chromatography (2% $CH_3OH$—$CH_2Cl_2$) gave 65 mg (8%) of the title compound: mp 102°-104°; NMR (pyridine-d$_5$, δ) 0.70-0.84(m, 2H), 1.00-1.25(m, 2H), 2.04(s, 3H), 2.10(m, 1H), 2.85(m, 1H), 3.12(m, 1H), 3.23(s, 3H), 3.51(bd, 1H, J=11 Hz), 3.99(dd, 1H, J=10, 4 Hz), 4.19(d, 1H, J=11 Hz), 5.03(t, 1H, J=10 Hz), 5.31(dd, 1H, J=10, 4 Hz), 10.17(bs, 1H); IR (KBr) 3420, 3320, 1700, 1580, 1430, 1330, 1210, 1056 cm$^{-1}$; UV ($CH_3OH$, λmax) 220, 330, 510 nm.

Anal. Calc'd for $C_{19}H_{22}N_4O_6$.3/4 $H_2O$: C, 55.00; H, 5.59; N, 13.50. Found: C, 55.16; H, 5.88; N, 12.86.

EXAMPLE 14

7-(Diethylthiophosphoryl)amino-9a-methoxymitosane (BL-6938)

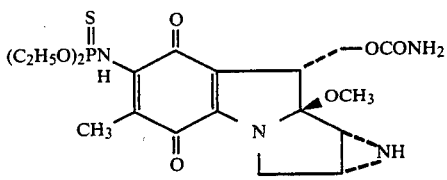

Starting with 450 mg (1.35 mmol) of mitomycin C, 2.7 mmol of NaH, and 280 mg (1.49 mmol) of diethylthiophosphoryl chloride, the reaction was carried out in a similar manner to Example 1. A silica gel column chromatography (2% $CH_3OH$—$CH_2Cl_2$) followed by a silica gel TLC (3% $CH_3OH$—$CH_2Cl_2$) gave 39 mg (8%) of 1a-diethylthiophosphoryl-7-(diethylthiophosphoryl)amino-9a-methoxymitosane (BL-6934): mp 47°-49°; NMR (pyridine-$d_5$, δ) 1.24(t, 6H, J=7 Hz), 2.31(d, 3H, J=1 Hz), 2.76(m, 1H), 3.14 (m, 1H), 3.22(s, 3H), 3.55(bd, 1H, J=10 Hz), 4.02 (dd, 1H, J=11, 4 Hz), 4.15-4.42(m, 5H), 5.04(t, 1H, J=11 Hz), 5.40(dd, 1H, J=11, 4 Hz), IR (KBr) 3450, 3350, 3210, 1720, 1640, 1625, 1580, 1425, 1320, 1015, 960, 810, 785 cm$^{-1}$; UV ($CH_3OH$, λmax) 212, 345, 515 nm.

Anal. Calc'd for $C_{23}H_{36}N_4O_9P_2S_2$: C, 43.26; H, 5.68; N, 8.77. Found: C, 43.29; H, 5.41; N, 8.83.

A more polar band gave 91 mg (14%) of the title compound: mp 76°-79°; NMR (pyridine-$d_5$, δ) 1.06-1.32(m, 12H), 2.28(d, 3H), J=1 Hz), 3.28(s, 3H), 3.30-3.76(m, 3H), 4.00-4.40(m, 10H), 4.72(t, 1H), J=11 Hz), 5.74(dd, 1H, J=11, 5 Hz); IR (KBr) 3450, 3280, 3210, 1715, 1620, 1575, 1425, 1325, 1015, 960, 780 cm$^{-1}$; UV ($CH_3OH$, λmax) 216, 348, 526 nm.

Anal. Calc'd for $C_{19}H_{27}N_4O_7PS$: C, 46.91; H, 5.60; N, 11.52. Found: C, 47.02; H, 5.53; N, 11.88.

EXAMPLE 15

$N^{1a}$-(Benzyloxycarbonyl)-7-benzyloxycarbonylamino-9a-methoxymitosane (BMY-25072)

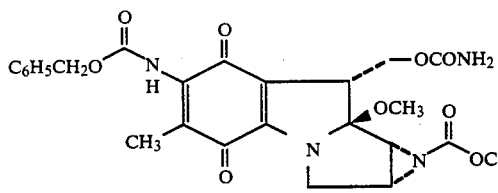

Starting with 668 mg (2 mmol) of mitomycin C, 4 mmol of NaH, and 997 mg (4 mmol) of benzyl N-hydroxysuccinimide carbonate, the reaction was carried out in a similar fashion as Example 7. A silica gel chromatography (2% $CH_3OH$—$CH_2Cl_2$) gave 490 mg (41%) of the title compound: mp 68°-70°; NMR (pyridine-$d_5$, δ) 2.09(s, 3H), 3.20(s, 3H), 3.42-3.60(m, 2H), 3.84(d, 1H, J=4 Hz), 4.08(dd, 1H, J=11, 5 Hz), 4.32(d, 1H, J=13 Hz), 4.86(t, 1H, J=11 Hz), 5.27(s, 2H), 5.36(s, 2H), 5.61(dd, 1H, J=11, 5 Hz), 7.24-7.55(m, 10H), 10.50(bs, 1H); IR (KBr) 3460, 3360, 1725, 1652, 1585, 1495, 1260, 1212, 1177, 1015 cm$^{-1}$.

Anal. Calc'd for $C_{31}H_{30}N_4O_9$: C, 61.79; H, 5.24; N, 9.63. Found: C, 61,68; H, 5.02, N, 9.30.

Substituting an $N^{1a}$-substituted analog of mitomycin C for mitomycin C as starting material in any of Examples 1-15 results in the production of products analagous to those of the examples and corresponding to those of Formula I wherein $R^1$ is lower alkyl. The $N^{1a}$-substituted mitomycin C starting materials may be obtained as described by Matsui et al., J. Antibiotics, 21, No. 3 189-198 (1968). Those compounds of Formula III wherein $R^1$ is a group as defined for $R^7$ are bis-substituted reaction products isolated from the foregoing examples as described. Under appropriately selected reaction conditions, the proportion of bis-product produced can be increased. Mitomycin C starting materials wherein the $N^{1a}$-substituent is an acyl group may be prepared as described by Matsui et al. in U.S. Pat. No. 3,450,705 patented June 17, 1969.

EXAMPLE 16

7-Acetylamino-9a-methoxy-1a-methylmitosane (BL-6916)

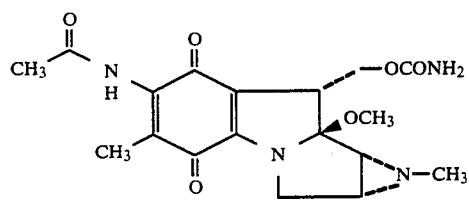

Starting with 348 mg (1 mmol) of porfiromycin, 2 mmol of NaH and 314 mg (2 mmol) of N-hydroxysuccinimide ester of acetic acid, the reaction was carried out similarly to Example 1. A silica gel preparative TLC (10% $CH_3OH$—$CH_2Cl_2$) gave 40 mg (10%) of the title compound: mp 101°-103°; NMR (pyridine-$d_5$, δ) 2.05(s, 3H), 2.14(dd, 1H, J=4, 2 Hz), 2.23(s, 3H), 2.27(s, 3H), 2.52(d, 1H, J=4 Hz), 3.16(s, 3H), 3.42 (dd, 1H, J=13, 2 Hz), 3.93(dd, 1H, J=12, 4 Hz), 4.08(d, 1H, J=13 Hz), 4.74(t, 1H, J=10 Hz), 5.24(dd, 1H, J=10, 4 Hz), 10.04(bs, 1H); IR (KBr) 3430, 3320, 1700, 1650, 1615, 1575, 1435, 1320, 1245, 1060 cm$^{-1}$; UV ($CH_3OH$, λmax) 221, 245(sh), 329, 515 nm.

Anal. Calc'd for $C_{18}H_{22}N_4O_6$ 0.5$H_2O$: C, 54.13; H, 5.80; N, 13.72. Found: C, 54.37; H, 5.71; N, 13.88.

EXAMPLE 17

7-[3-(Ethoxycarbonyl)propionyl]amino-9a-methoxymitosane (BL-6920)

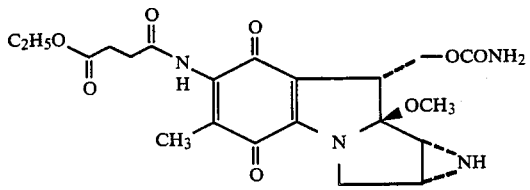

Starting with 334 mg (1 mmol) of mitomycin C, 2 mmol of NaH, and 486 mg (2 mmol) of N-hydroxysuccinimide ester of monoethyl succinate, the reaction was carried out similarly to Example 1. An alumina chromatography (2% $CH_3OH$—$CH_2Cl_2$) gave 130 mg (30%) of the title compound: mp 52°-55°; NMR (pyridine-$d_5$, δ) 1.12(t, 3H), 2.08(s, 3H), 2.68-3.16(m, 6H), 3.22(s, 3H), 3.52(bd, 1H, J=13 Hz), 4.00(dd, 1H, J=10, 4 Hz), 4.12(q, 2H, J=7 Hz), 4.16(d, 1H, J=13 Hz), 5.06(t, 1H, J=10 Hz), 5.35(dd, 1H, J=10, 4 Hz); IR (KBr) 3455, 3310, 1720, 1660, 1625, 1580, 1450, 1340, 1300, 1220, 1070 cm$^{-1}$; UV (CH$_3$OH, λmax) 220, 240(sh), 334, 515 nmr.

Anal. Calc'd for C$_{20}$H$_{26}$N$_4$O$_7$0.75H$_2$O: C, 52.61; H, 6.19; N, 12.51. Found: C, 53.99; H, 5.69; N, 12.12.

EXAMPLE 18

7-Benzoylamino-9a-methoxymitosane (BL-6930)

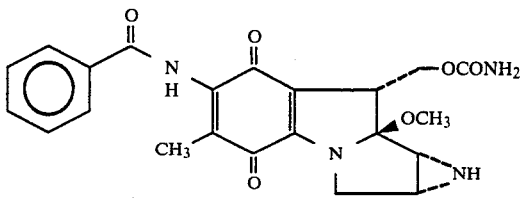

Starting with 668 mg (2 mmol) of mitomycin C, 4 mmol of NaH, and 730 mg (3 mmol) of p-nitrophenyl benzoate, the reaction was carried out similarly to Example 1. An alumina chromatography (2% CH$_3$OH—CH$_2$Cl$_2$) gave 150 mg (17%) of the title compound: mp 129°-130°; NMR (pyridine-d$_5$, δ) 2.12(s, 3H), 2.80(m, 1H), 3.18(m, 1H), 3.25(s, 3H), 3.54(bd, 1H, J=13 Hz), 4.01(dd, 1H, J=10, 4 Hz), 4.23(d, 1H, J=13 Hz), 5.04(t, 1H, J=10 Hz), 5.33(dd, 1H, J=10, 4 Hz), 10.00(bd, 1H); IR (KBr) 3460, 3360, 3210, 1715, 1660, 1640, 1585, 1480, 1260, 1070 cm$^{-1}$; UV (CH$_3$OH, λmax) 215, 236(sh), 337, 515 nm.

Anal. Calc'd for C$_{22}$H$_{22}$N$_4$O$_6$.H$_2$O: C, 57.89; H, 5.29; N, 12.27. Found: C, 57.71; H, 5.29; N, 12.27.

EXAMPLE 19

7-[((2-Chloroethyl)amino)carbonyl]amino-9a-methoxymitosane (BL-6931)

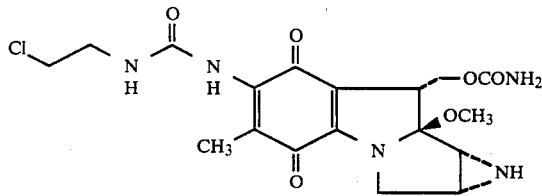

Starting with 334 mg (1 mmol) of mitomycin C, 2 mmol of NaH, and 211 mg (2 mmol) of 2-chloroethyl isocyanate, the reaction was carried out similarly to Example 10. An alumina column chromatography (3% CH$_3$OH—CH$_2$Cl$_2$) gave 50 mg (11%) of the title compound: mp 118°-120°; NMR (pyridine-d$_5$, δ) 2.30(s, 3H), 2.73(m, 1H), 3.13(m, 1H), 3.20(s, 3H), 3.64(bd, 1H, J=13 Hz), 3.80(m, 4H), 3.96dd, 1H, J=10, 4 Hz), 4.23(d, 1H, J=13 Hz), 5.02(t, 1H, J=10 Hz), 5.28(dd, 1H, J=10, 4 Hz), 7.80(bs, 1H), 8.46(bt, 1H); IR (KBr) 3410, 3300, 1720, 1620, 1560, 1440, 1330, 1220, 1055 cm$^{-1}$; UV (CH$_3$OH, λmax) 218, 238(sh), 296, 345, 520 nm.

Anal. Calc'd for C$_{18}$H$_{22}$ClN$_5$O$_6$ 0.5H$_2$O: C, 48.16; H, 5.16; N, 15.60. Found: C, 48.21; H, 5.16; N, 15.27.

Similarly isopropylisothiocyanate may be substituted in Example 10 for isopropylisocyanate and 7-(isopropylaminothiocarbonyl)amino-9a-methoxymitosane produced substantially as described.

We claim:

1. A compound having the formula

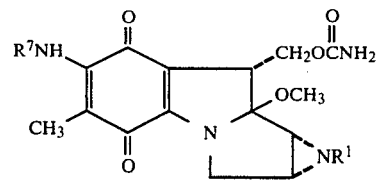

wherein

R$^1$ is selected from H, C$_{1-6}$ alkyl, and R$^7$,

R$^7$ is selected from

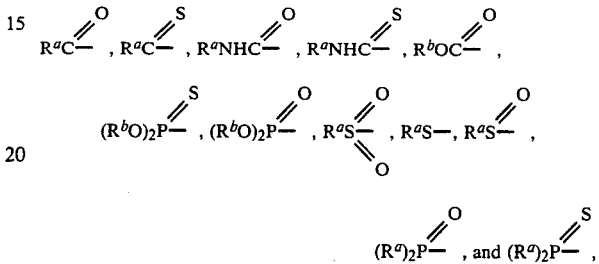

wherein

R$^a$ is selected from H, C$_{1-6}$ alkyl, A-substituted C$_{1-6}$ alkyl, C$_{6-10}$ aryl, A-substituted C$_{6-10}$ aryl, C$_{7-17}$ aralkyl, A-substituted C$_{7-17}$ aralkyl, C$_{2-6}$ alkenyl, A-substituted C$_{2-6}$ alkenyl, C$_{2-6}$ alkynyl, A-substituted C$_{2-6}$ alkynyl, C$_{3-8}$ cycloalkyl, C$_{4-10}$ cycloalkylalkyl, R$^b$ is selected from the group consisting of C$_{1-6}$ alkyl, A-substituted C$_{1-6}$ alkyl, C$_{6-10}$ aryl, A-substituted C$_{6-10}$ aryl, C$_{7-17}$ aralkyl and A-substituted C$_{7-17}$ aralkyl, wherein said A substituent is selected from the group consisting of chlorine, bromine, fluorine, iodine, amino, tert.-beoxycarbonylamino, C$_{1-6}$ alkoxy, C$_{1-6}$ alkylamino, di(C$_{1-6}$)alkylamino, C$_{3-8}$ cycloalkylamino, C$_{4-14}$ cycloalkylamino, thiol, C$_{1-6}$ alkylthio, C$_{1-6}$ alkyldithio, C$_{6-10}$ arylthio, and C$_{7-17}$ aralkylthio.

2. The compound of claim 1 where R$^1$ is H.

3. The compound of claim 1 where R$^1$ is H and R$^7$ is alkanoyl having from 1 to 7 carbon atoms.

4. The compound of claim 1, 7-(formyl)amino-9a-methoxymitosane.

5. The compound of claim 1, 7-(trifluoroacetyl)amino-9a-methoxymitosane.

6. The compound of claim 1, 7-acetamido-9a-methoxymitosane.

7. The compound of claim 1, 7-(2-chloroacetyl)amino-9a-methoxymitosane.

8. The compound of claim 1, 7-(methanesulfonyl)amino-9a-methoxymitosane.

9. The compound of claim 1, 7-[3-(tert.-butoxycarbonylamino)propionyl]amino-9a-methoxymitosane.

10. The compound of claim 1, 7-(methoxycarbonyl)amino-9a-methoxymitosane.

11. The compound of claim 1, 7-(ethoxycarbonyl)amino-9a-methoxymitosane.

12. The compound of claim 1, 7-[(2-methoxyethoxy)carbonyl]amino-9a-methoxymitosane.

13. The compound of claim 1, 7-(isopropylaminocarbonyl)amino-9a-methoxymitsane.

14. The compound of claim 1, 7-(cyclohexylaminocarbonyl)amino-9a-methoxymitosane.

15. The compound of claim 1, 7-(benzylaminocarbonyl)amino-9a-methoxymitosane.

16. The compound of claim 1, 7-(diethylthiophosphoryl)amino-9a-methoxymitosane.

17. The compound of claim 1, $N^{1a}$-(benzyloxycarbonyl)-7-benzyloxycarbonylamino-9a-methoxymitosane.

18. The compound of claim 1 wherein $R^1$ is H, and $R^7$ is cycloalkylcarbonyl having 4 to 9 carbon atoms.

19. The compound of claim 1, 7-(Cyclopropanecarbonyl)amino-9a-methoxymitosane.

20. The compound of claim 1, 7-acetylamino-9a-methoxy-1a-methylmitosane.

21. The compound of claim 1, 7-[3-(ethoxycarbonyl)propionyl]amino-9a-methoxymitosane.

22. The compound of claim 1, 7-benzoylamino-9a-methoxymitosane.

23. The compound of claim 1, 7-[((2-chloroethyl)aminocarbonyl]amino-9a-methoxymitosane.

* * * * *